United States Patent
Ozawa et al.

(10) Patent No.: US 9,644,165 B2
(45) Date of Patent: May 9, 2017

(54) LUBRICATING RESIN COMPOSITION

(71) Applicant: Sumitomo Seika Chemicals Co., Ltd., Kako-gun, Hyogo (JP)

(72) Inventors: Hitoshi Ozawa, Osaka (JP); Shinichi Takemori, Himeji (JP); Tsuyoshi Masuda, Himeji (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 56 days.

(21) Appl. No.: 14/419,688

(22) PCT Filed: Jul. 26, 2013

(86) PCT No.: PCT/JP2013/070363
§ 371 (c)(1),
(2) Date: Feb. 5, 2015

(87) PCT Pub. No.: WO2014/024706
PCT Pub. Date: Feb. 13, 2014

(65) Prior Publication Data
US 2015/0184106 A1  Jul. 2, 2015

(30) Foreign Application Priority Data
Aug. 10, 2012 (JP) .................. 2012-178432

(51) Int. Cl.
*C10M 107/44* (2006.01)
*C10M 107/24* (2006.01)
(Continued)

(52) U.S. Cl.
CPC ......... *C10M 107/44* (2013.01); *A61L 29/049* (2013.01); *A61L 29/14* (2013.01);
(Continued)

(58) Field of Classification Search
CPC . C10M 107/44; C10M 2209/04; C08L 77/02; C08L 77/06; C08G 18/4833;
(Continued)

(56) References Cited

U.S. PATENT DOCUMENTS 4,170,821 A    10/1979  Booth
5,415,791 A *   5/1995  Chou ................... C10M 169/04
                                                    508/103
(Continued)

FOREIGN PATENT DOCUMENTS

EP    2447325 A1    5/2012
JP    54-094961 A   7/1979
(Continued)

OTHER PUBLICATIONS

Notification of Transmittal of Translation of The International Preliminary Report on Patentability (Form PCT/IB/338) of International Application No. PCT/JP2013/070363 mailed Feb. 19, 2015 with Forms PCT/IB/373 and PCT/ISA/237 (9 pages).
(Continued)

*Primary Examiner* — James Goloboy
(74) *Attorney, Agent, or Firm* — Westerman, Hattori, Daniels & Adrian, LLP

(57) ABSTRACT

The present invention provides a lubricating resin composition for personal care, wherein the composition not only maintains its excellent lubricity and roughness-resistant property under a wet condition even during repeated use thereof, but also represents a low swelling ratio and no slimy feeling under a wet condition. The lubricating resin composition for personal care Of the present invention comprises 100 parts by mass of a water-absorbent modified polyalkylene oxide and 25 to 500 parts by mass of a low-melting point polyamide resin.

4 Claims, 1 Drawing Sheet

(51) Int. Cl.
    *C08G 18/48*    (2006.01)
    *C08G 18/66*    (2006.01)
    *C08L 77/02*    (2006.01)
    *C08L 77/06*    (2006.01)
    *A61L 29/14*    (2006.01)
    *A61L 29/04*    (2006.01)

(52) U.S. Cl.
    CPC ....... *C08G 18/485* (2013.01); *C08G 18/4833* (2013.01); *C08G 18/6674* (2013.01); *C08L 77/02* (2013.01); *C08L 77/06* (2013.01); *A61L 2400/10* (2013.01); *C10M 2209/04* (2013.01)

(58) Field of Classification Search
    CPC .............. C08G 18/485; C08G 18/6674; A61L 29/14049; A61L 2400/10
    USPC ........................................................ 508/386
    See application file for complete search history.

(56) References Cited

U.S. PATENT DOCUMENTS

| | | | |
|---|---|---|---|
| 5,468,221 | A | 11/1995 | Schöner |
| 5,626,154 | A | 5/1997 | Rogers et al. |
| 6,054,504 | A | 4/2000 | Dalla Riva Toma |
| 2003/0008782 | A1 | 1/2003 | Endou et al. |
| 2004/0019133 | A1 | 1/2004 | Saito et al. |
| 2004/0082701 | A1 | 4/2004 | Ota et al. |
| 2004/0127646 | A1 | 7/2004 | Duan et al. |
| 2005/0209428 | A1 | 9/2005 | Tamareselvy |
| 2012/0094880 | A1* | 4/2012 | Ozawa ............... C08G 18/0895 508/583 |

FOREIGN PATENT DOCUMENTS

| | | | | |
|---|---|---|---|---|
| JP | 04-507054 | A | 12/1992 | |
| JP | 07-024156 | A | 1/1995 | |
| JP | 09-502632 | A | 3/1997 | |
| JP | 10-248919 | A | 9/1998 | |
| JP | 10-248921 | A | 9/1998 | |
| JP | 2001-527027 | A | 12/2001 | |
| JP | 2004-509207 | A | 3/2004 | |
| JP | 2008-540647 | A | 11/2008 | |
| JP | WO 2010150875 | A1 * | 12/2010 | ......... C08G 18/0895 |
| WO | 02/30365 | A1 | 4/2002 | |

OTHER PUBLICATIONS

Notification Concerning Transmittal of International Preliminary Report on Patentability (Form PCT/IB/326) of International Application No. PCT/JP2013/070363 mailed Feb. 19, 2015 with Forms PCT/IB/373 and PCT/ISA/237 (in Japanese) (7 pages).
Extended European Search Report dated Feb. 16, 2016, issued in counterpart European Application No. 13827485.7 (8 pages).
International Search Report dated Oct. 1, 2013, issued in corresponding application No. PCT/JP2013/070363.

* cited by examiner

LUBRICATING RESIN COMPOSITION

TECHNICAL FIELD

The present invention relates to a lubricating resin composition whose lubricity is achieved under a wet condition, especially, a lubricating resin composition for use in personal care items to be used in contact with a skin. The present invention more particularly relates to a lubricating resin composition for personal care obtained by mixing a water-absorbent modified polyalkylene oxide with a low-melting point polyamide resin.

BACKGROUND ART

For a personal care item such as a razor, a razor blade cartridge has conventionally been proposed, which comprises a shaving aid containing a water-soluble resin such as a polyalkylene oxide attached to a portion of the razor blade cartridge made of plastic, in order to reduce the resistive force between a portion of a razor and the facial surface, etc., (for example, Patent Document 1).

It is known that a high-molecular weight compound (water-soluble resin) obtained by reacting a polyalkylene oxide compound and a diisocyanate with each other and having a weight-average molecular weight of 10000 or higher is used as a water-soluble solidified shaving aid (Patent Document 2).

A composite may be used as a smoother (lubricating agent) for wet shaving, wherein the composite comprises a water-swellable polymer swelling and releasing various aids upon immersion of the composite in water due to mixing of a water-soluble polymer (water-soluble resin) and the water-swellable polymer (Patent Document 3).

A polymer composite is disclosed as a polymer composite used in wet shaving instruments, medical instruments, etc., wherein the polymer composite comprises a water-insoluble polymer, and a water-sensitive copolymer (water-soluble resin) obtained by polymerizing an alkylene oxide monomer and an epoxy-functional monomer (Patent Document 4).

PRIOR ART DOCUMENT

Patent Documents

Patent Document 1: JP 54-94961 A
Patent Document 2: JP 07-24156 A
Patent Document 3: JP 09-502632 A
Patent Document 4: JP 2004-509207 A

SUMMARY OF THE INVENTION

Problem to be Solved

The razor blade cartridge described in Patent Document 1, the composite described in Patent Document 3, and the polymer composite described in Patent Document 4 each utilize elution of the water-soluble resin under a wet condition to give lubricity to the surfaces of the cartridge.

However, when a desired member is formed by melt-mixing the water-soluble resin and a thermoplastic resin, the water-soluble resin is scattered in blocks in the surface of the member since the compatibility between the water-soluble resin and the thermoplastic resin is low. For this reason, lubricity at the initial stage of use is excellent while the scattered water-soluble resin is dropped in blocks by repeated use, and the lubricity is lost in a short time.

The shaving aid described in Patent Document 2 and comprising the high-molecular weight compound is excellent in water-solubility, and the water-soluble component thereof therefore flows out at one time by an amount equal to or more than a necessary amount. Thus, the following problems arise: that the skin becomes slimy; that the water-soluble component of the compact drops off to cause contraction and hardening during repeated use thereof resulting in degradation of the durability thereof; and the like. Although mixing with another resin is also examined in order to improve durability, another problem arises that the compatibility therebetween is low.

A water-soluble resin such as a polyalkylene oxide generally has more excellent lubricity as the molecular weight thereof increases, while cobwebbing thereof under a wet condition becomes more remarkable and the melt viscosity thereof becomes higher. Thus, it is necessary to raise the temperature for the processing. For this reason, the high-molecular weight water-soluble resin is often mixed with a polymer having a low hydrophilic property and low flexibility such as high impact polystyrene or polystyrene each having a high processing temperature. The mixture thus obtained is excellent in lubricity under a wet condition, while high impact polystyrene or polystyrene themselves do not adapt to water and have low flexibility, causing therefore problems to arise that the composition has low adhesiveness to the skin and that a roughness resistant property thereof is degraded because feeling of roughness is generated on the surface thereof due to the dropping off of the water-soluble resin component during repeated use. When the water-soluble resin is increased in order to maintain the good lubricity, the swelling ratio under a wet condition is increased, and thus, when the composition is then dried in the repeated use, another problem arises that the surface of the composition is deformed to have recesses and protrusions.

On the other hand, a resin which is familiar with water and represents a good touch can be highly hydrophilic nylon, but the processing temperature of general nylons are high compared with those of high impact polystyrene and polystyrene. Thus, when nylon and a polyalkylene oxide are simultaneously used, the polyalkylene oxide is decomposed during the processing and becomes colored, and the molecular weight thereof is reduced. A problem therefore arises that the lubricity thereof is degraded, and the like. In order to solve this problem, it is also examined to mix low-melting point nylon with a high-molecular weight polyalkylene oxide. However, the high-molecular weight polyalkylene oxide has high melt viscosity, and a problem arises in their compatibility that the high-molecular weight polyalkylene oxide does not sufficiently dissolve at the mixing temperature in its mixing with low-melting point nylon, and only disperses in the form of dispersed powders in low-melting point nylon, resulting in difficulty for the effect (lubricity) to be achieved, etc.

An object of the present invention is to provide a lubricating resin composition for personal care, wherein the composition not only maintains its excellent lubricity and roughness resistant property under a wet condition even during repeated use thereof, but also has a low swelling ratio and represents no slimy feeling under a wet condition.

Means to Solve the Problems

The inventors has actively studied to solve the above problems, and as a result, found that a lubricating resin composition comprising a water-absorbent modified polyalkylene oxide and a specific polyamide resin mixed therein was excellent in lubricity and roughness resistant property and represented good deformation resistance under a dry condition, and the inventors has achieved the present invention.

The present invention relates to a lubricating resin composition for personal care, wherein the composition comprises 100 parts by mass of a water-absorbent modified polyalkylene oxide and 25 to 500 parts by mass of a low-melting point polyamide resin.

Effect of the Invention

The lubricating resin composition of the present invention can maintain its excellent lubricity and roughness resistant property under a wet condition even during repeated use thereof. In addition, the lubricating resin composition of the present invention represents a good deformation resistance under a dry condition due to its relatively low swelling ratio under a wet condition. Furthermore, the lubricating resin composition of the present invention represents no slimy feeling under a wet condition. The lubricating resin composition of the present invention comprises the low-melting point polyamide, and therefore represents a good touch having a moist feeling even under a dry condition. As a result, the lubricating resin composition of the present invention is widely usable for personal care items such as wet shaving instruments typified by a razor, and medical instruments such as a catheter.

MODES FOR CARRYING OUT THE INVENTION

Figure 1:
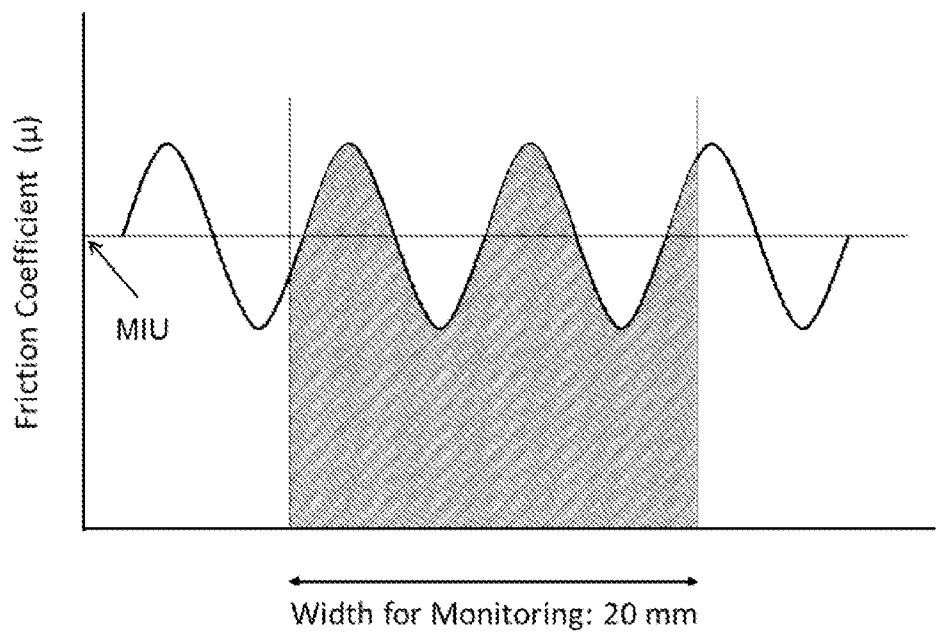
FIG. 1 is a schematic diagram of a method of determining a mean coefficient of friction (MIU).

The lubricating resin composition of the present invention comprises a water-absorbent modified polyalkylene oxide and a low-melting point polyamide resin.

The water-absorbent modified polyalkylene oxide used in the lubricating resin composition of the present invention is, for example, a modified polyalkylene oxide obtained by reacting a polyalkylene oxide compound, a diol compound and a diisocyanate compound with each other. The water-absorbent modified polyalkylene oxide has low melt viscosity and is thermoplastic. The water-absorbent modified polyalkylene oxide thus has good compatibility with a polyamide resin, compared with water-soluble resins such as a polyalkylene oxide.

The polyalkylene oxide compound for producing the water-absorbent modified polyalkylene oxide is a homopolymer or a copolymer comprising one, or two or more type (s) of alkylene oxide group selected from the group consisting of preferably alkylene oxide groups having 2 to 9 carbon atoms and more preferably alkylene oxide groups having 2 to 4 carbon atoms. Preferable specific examples of the alkylene oxide group include ethylene oxide, 1,2-propylene oxide, 1,3-propylene oxide, isobutylene oxide, 1,2-butylene oxide, 2,3-butylene oxide, 1,3-butylene oxide, trimethylethylene oxide, tetramethylethylene oxide, cyclohexene oxide, oxetane, tetrahydrofuran, tetrahydropyran, 1,2-pentene oxide and 1,2-hexene exide. The polyalkylene oxide compound may be used alone, and two or more types thereof may also be used in combination.

The polyalkylene oxide compound is preferably a polyalkylene oxide compound comprising 90% by mass or more of ethylene oxide groups and more preferably a polyalkylene oxide compound comprising 95% by mass or more of ethylene oxide groups, from the viewpoint of further improvement in lubricity of the lubricating resin composition in the initial state. Each of these ratios is a value relative to the overall weight of the polyalkylene oxide compound.

The polyalkylene oxide compound is preferably a polyalkylene oxide compound having a number average molecular weight of 5000 to 50000, and more preferably a polyalkylene oxide compound having a number average molecular weight of 10000 to 30000, from the viewpoint of further improvement in lubricity of the lubricating resin composition in the initial state and during its repeated use.

The dial compound for producing the water-absorbent modified polyalkylene oxide is one, or two or more type(s) of diol selected from the group consisting of preferably dials having 2 to 9 carbon atoms and more preferably dials having 2 to 5 carbon atoms. Specific examples of the dial compound include aliphatic diol compounds such as ethylene glycol, diethylene glycol, triethylene glycol, tetraethylene glycol, propylene glycol, dipropylene glycol, trimethylene glycol, 1,3-butanediol, 2,3-butanediol, 1,4-butanediol, 1,5-pentanediol, 1,6-hexanediol and 1,9-nonanediol. Among these diol compounds, ethylene glycol and 1,4-butanediol are suitably used from the viewpoints that the obtained water-absorbent modified polyalkylene oxide is excellent in water absorption ability, that elution of a water-soluble component therefrom is suppressed, and that stability thereof is excellent. The dial compound may be used alone, and two or more types thereof may also be used in combination.

The used amount of the diol compound preferably is from 0.8 to 2.5 mol and more preferably from 1.0 to 2.0 mol, relative to 1 mol of the polyalkylene oxide compound, from the viewpoint of water absorption ability of the water-absorbent modified polyalkylene oxide. The molar number of the polyalkylene oxide compound can be determined by dividing the mass thereof by the number average molecular weight thereof.

The diisocyanate compound is not particularly limited only when the diisocyanate compound is a compound having two isocyanate groups (—NCO) in one same molecule. Examples thereof include aromatic diisocyanates such as 4,4'-diphenylmethane diisocyanate (MDI), 1,8-dimethylbenzol-2,4-diisocyanate and 2,4-tolylene diisocyanate (TDI); aliphatic diisocyanates such as 1,6-hexamethylene diisocyanate (HDI); and alicyclic diisocyanate such as dicyclohexylmethane-4,4'-diisocyanate (HMDI) and 3-isocyanatomethyl-3,5,5-trimethylcyclohexyl isocyanate (IPDI). Among these diisocyanate compounds, aliphatic diisocyanates and alicyclic diisocyanates are suitably used from the viewpoints of the compatibility with polyamide resins, suppression of elution of a water-soluble compound, and excellent stability, and dicyclohexylmethane-4,4'-diisocyanate (HMDI) and 1,6-hexamethylene diisocyanate (HDI) are more suitably used. The diisocyanate compound may be used alone, and two or more types thereof may also be used in combination.

The ratio in use of each of the polyalkylene oxide compound, the diol compound, and the diisocyanate compound is determined such that the ratio of the molar number of isocyanate groups of the diisocyanate compound relative to the total molar number of terminal hydroxyl groups of the polyalkylene oxide compound and hydroxyl groups of the diol compound [R value=(—NCO group/—OH group)] is preferably in a range of 0.7 to 1.2 and more preferably in a range of 0.8 to 1.05, from the viewpoint of further improvement in each of the lubricity during repeated use, and the compatibility between the water-absorbent modified polyalkylene oxide and the polyamide resin. The molar number of the isocyanate groups of the diisocyanate compound can be determined by doubling the value obtained by dividing the mass of the diisocyanate compound by its number average molecular weight.

Examples of methods of reacting the polyalkylene oxide compound, the dial compound and the diisocyanate compound with each other include a method of dissolving or dispersing all the compounds in a reaction solvent such as toluene, xylene or dimethylformamide to cause the compounds to react; and a method of uniformly mixing all the compounds in a powder state or a solid state, and then heating the mixture to a predetermined temperature to cause the compounds to react in a molten state. From the viewpoint of the industrial implementation, preferable is a method of continuously supplying the raw materials in the molten state, and mixing the raw materials in a multi-screw extruder to cause the raw materials to react. The temperature of the reaction is preferably from 70 to 210° C.

When the water-absorbent modified polyalkylene oxide is produced, from the viewpoint of promoting the reaction, a small amount of triethylamine, triethanolamine, dibutyltin dilaurate, dioctyltin dilaurate, tin 2-ethylhexanoate, triethylenediamine or the like may also be added to the reaction system.

Thus, the water-absorbent modified polyalkylene oxide can be obtained by reacting the polyalkylene oxide compound, the diol compound and the diisocyanate compound. A urethane group is formed in the water-absorbent modified polyalkylene oxide from the reaction between an isocyanate group and a hydroxyl group, and an interaction acts between the urethane group and an amide group of the low-melting point polyamide resin described later. Thereby, the compatibility is improved between the water-absorbent modified polyalkylene oxide and the low-melting point polyamide resin. It can be considered that excellent lubricity and roughness resistant property during the repeated use, the relatively low swelling ratio under a wet condition, and the good deformation resistance under a dry condition are achieved due to this improvement of the compatibility.

The water absorption ability of the water-absorbent modified polyalkylene oxide used in the lubricating resin composition of the present invention is preferably from 10 to 40 [g/g], and more preferably from 15 to 35 [g/g]. If the water absorption ability of the water-absorbent modified polyalkylene oxide is lower than 10 [g/g], the lubricity and the roughness resistant property in the initial stage of use of and during repeated use of the obtained lubricating resin composition may be degraded. If the water absorption ability of the water-absorbent modified polyalkylene oxide is higher than 40 [g/g], the degree of maintenance of the lubricity may be lowered during repeated use of the obtained lubricating resin composition. The "water absorption ability" in the present invention is a value measured using a method described later.

The ratio of the water-soluble component of the water-absorbent modified polyalkylene oxide used in the present invention is preferably from 5 to 30% by mass and more preferably from 10 to 20% by mass, relative to the mass of the water-absorbent modified polyalkylene oxide, from the viewpoint of improving lubricity of the obtained lubricating resin composition. The "ratio of the water-soluble component" in the present invention is a value measured by a method described later.

From the viewpoint of further improvement of each of the initial lubricity and the compatibility with the polyamide resin, the melt viscosity of the water-absorbent modified polyalkylene oxide used in the lubricating resin composition of the present invention is preferably from 100 to 800 [Pa·s] and more preferably from 100 to 400 [Pa·s] when the melt viscosity is measured by means of a flow tester (constant test force extrusion type capillary rheometer) (conditions: 170° C., 5.0 MPa, a die having a diameter of 1 mm×a length of 1 mm is used). In this case, the melt viscosity ratio with the melt viscosity of the low-melting point polyamide resin (under the same conditions) (the low-melting point polyamide resin/the water-absorbent modified polyalkylene oxide) is preferably from 0.1 to 0.8, and more preferably from 0.2 to 0.6.

The low-melting point polyamide resin used in the lubricating resin composition of the present invention is preferably a polyamide resin having a melting point of 160° C. or lower. If a polyamide resin having a melting point higher than 160° C. (nylon) is used, the water-absorbent modified polyalkylene oxide tends to be modified during the mixing, and the lubricating resin composition may be obtained which does not have good lubricity from the initial stage. More preferably, the melting point thereof is from 80 to 150° C.

Preferably, the low-melting point polyamide resin having a melting point of 160° C. or lower is a polyamide obtained by polymerizing at least one type of raw material for a polyamide selected from the group consisting of nylon 6 (polycaprolactam), nylon 66 (polyhexamethyleneadipamide), nylon 610 (polyhexamethylenesebacamide), nylon 11 (polyundecaneamide), and nylon 12 (polylauryllactam). More preferably, a polyamide is used which is obtained by copolymerizing at least two types of the above raw materials for polyamide, and example of the copolymerized polyamide include binary copolymers such as nylon 6/nylon 12 ("/" indicates that the material is a copolymer) and nylon 610/nylon 12, ternary copolymers such as nylon 6/nylon 66/nylon 12, nylon 6/nylon 610/nylon 12 and nylon 66/nylon 610/nylon 12, and a multicomponent copolymer such as nylon 6/nylon 66/nylon 610/nylon 12. The low-melting point polyamide resin may be a polyamide obtained by copolymerizing the above raw material for polyamide and a raw material including a raw material different from the above raw materials for polyamide. The low-melting point polyamide resin may be used alone, and two or more types thereof may also be used in combination. The specific names of commercially available products as the low-melting point polyamide resin can be "Amilan 842P-48", "Amilan 842P-70" and "Amilan 842P-80" (manufactured by Toray Industries, Inc.), and also "Griltex D1500A" and "Griltex D1666A" (manufactured by EMS Japan, Ltd.). The "melting point" refers to a melting peak temperature (° C.) measured by means of a differential scanning calorimeter (DSC) at a temperature increase rate of 10° C./min.

The melt viscosity of the low-melting point polyamide resin is preferably from 60 to 300 [Pa·s] and more preferably 50 to 150 [Pa·s], the melt viscosity being measured by means of a flow tester (constant test force extrusion type capillary rheometer) (conditions: 170° C., 5.0 MPa, a die having a diameter of 1 mm×a length of 1 mm is used).

The melt flow rate (MFR) of the low-melting point polyamide resin (conditions: 160° C., 21.18 N) is preferably from 10 to 120 [g/min] and more preferably from 15 to 100 [g/min].

The ratio of the used low-melting point polyamide resin is 25 parts by mass or higher and preferably 50 parts by mass or higher, relative to 100 parts by mass of the water-absorbent modified polyalkylene oxide. The ratio of the used low-melting point polyamide resin is 500 parts by mass or lower, and preferably 400 parts by mass or lower, relative to 100 parts by mass of the water-absorbent modified polyalkylene oxide. For example, the ratio of the used low-melting point polyamide resin is from 25 to 500 parts by mass and preferably from 50 to 400 parts by mass, relative to 100 parts by mass of the water-absorbent modified polyalkylene oxide.

In the case where the ratio of the used low-melting point polyamide resin is less than 25 parts by mass, if the obtained lubricating resin composite is brought into contact with water, the swelling ratio for water is high and the dimensions are significantly varied by the swelling. Thereafter, when the lubricating resin composition is dried during the repeated use, the surface of the composition is deformed to have protrusions and recesses. In the case where that the ratio of the used low-melting point polyamide resin exceeds 500 parts by mass, lubricity of the obtained lubricating resin composition is degraded in the initial stage.

In addition to the low-melting point polyamide resin, other polymers having good compatibility with the water-absorbent modified polyalkylene oxide may be also used, such as an ethylene/vinyl acetate copolymer, an ethylene/acrylic acid copolymer and an ethylene/ethyl acrylate copolymer. Simultaneous use of these copolymers improves flexibility of the obtained lubricating resin composition. The ratio of the other polymer used therein is 500 parts by mass or lower and preferably from 100 to 300 parts by mass, relative to 100 parts by mass of the water-absorbent modified polyalkylene oxide.

Examples of a method of producing the lubricating resin composition of the present invention include 1) a method wherein the water-absorbent modified polyalkylene oxide, the low-melting point polyamide resin and optionally the other polymer are used each by a predetermined amount and mixed in advance by means of a mixing machine such as a Henschel mixer or a blender and, then the mixture is supplied to a kneader, a roll, an extruder or the like, and is melt-mixed; 2) a method wherein the water-absorbent modified polyalkylene oxide, the low-melting point polyamide resin and optionally the other polymer are each supplied by a predetermined amount to a kneader, a roll, an extruder or the like by means of a metering feeder or the like, and are melt-mixed; and 3) a method wherein the polyalkylene oxide compound, the diol compound and the diisocyanate compound are caused to react with each other in the low-melting point polyamide resin melted in advance.

A twin-screw extruder is suitably used as the machine for performing the melt-mixing process, the melting process and/or the reaction process, from the viewpoint of its excellent mixability for the components.

After the melt-mixing process or the reaction process, the mixture may be also molded into a desired shape such as a pellet, a sheet, a bar or a fiber by executing injection molding or extrusion molding. The lubricating resin composition of the present invention may thus have the figure of a raw material such as a pellet or may have the figure of a desired compact such as a sheet, a bar or a fiber.

When the lubricating resin composition according to the present invention is produced, a stabilizer may be also added from the viewpoint of preventing resolution of each of the components and the obtained lubricating resin composition; a UV absorber may be also added from the viewpoint of improving the weather resistance of the obtained lubricating resin composition; a pigment, a coloring material or the like may be also added from the viewpoint of coloring the obtained lubricating resin composition; and a soap basis or the like may be also added from the viewpoint of imparting foamability to the obtained lubricating resin composition.

In addition, water-soluble polyalkylene oxide may be also added from the viewpoint of improving the adhesiveness to the skin. Water-soluble polyalkylene oxide is excellent in the compatibility with the water-absorbent modified polyalkylene oxide, and can therefore be uniformly dispersed even at a processing temperature of the low-melting point polyamide resin (low processing temperature).

The lubricating resin composition of the present invention is useful for applications in which achievement of lubricity under a wet condition is necessary, and is useful for personal care applications such as wet shaving instruments typified by a razor, and medical instruments such as a catheter.

For example, when the lubricating resin composition of the present invention is used in a wet shaving instrument (razor), the lubricating resin composition constitutes a so-called shaving aid unit which is arranged in substantially parallel to a razor blade in a face for attaching the razor blade in the razor or its cartridge (hereinafter, referred to as "razor or the like"). Thereby, the razor or the like comprising the lubricating resin composition of the present invention can maintain its excellent lubricity and roughness resistant property under a wet condition even during its repeated use. The shaving aid unit in the razor or the like has relatively low swelling ratio under a wet condition, and thus represents a good deformation resistance under a dry condition. The shaving aid unit represents no slimy feeling under a wet condition. The shaving aid unit comprises the low-melting point polyamide resin having high hydrophilicity, and thus represents moist and good touch feeling, and good feeling to skin even under a dry condition.

For example, when the lubricating resin composition of the present invention is used in a catheter, the lubricating resin composition is arranged on the surface of a stent or a guide wire used for a resin in contact with a living tissue in the catheter. Thereby, the catheter with the lubricating resin composition of the present invention achieves the same effect as achieved when the lubricating resin composition is used in the shaving aid unit of the razor or the like.

EXAMPLES

The present invention will be described below in further detail by Examples and Comparative Examples. However, the present invention is not limited to these.

[Evaluation Methods]

Measurement and evaluation were executed according to the following methods for the water absorption ability, the ratio of the water-soluble component, and the melt viscosity of the water-absorbent modified polyalkylene oxide described in each of Production Examples, and the swelling ratio, the thickness variation, the slimy feeling and the friction physical property of the lubricating resin composition obtained in each of Examples and Comparative Examples.

(1) Water Absorption Ability

The water absorption ability of the water-absorbent modified polyalkylene oxide was measured using the following method.

About 1 [a] of the water-absorbent modified polyalkylene oxide (in a pellet form) was weighed (A [g]), and then was immersed in 100 [mL] of ion exchange water measured in a 200-mL beaker under room temperature (22° C.) for 24 hours to gel. The gel was then filtered using a 200-mesh wire gauze (pore size: 75 μm) and the mass thereof (B [g]) was measured. The water absorption ability was calculated according to the following formula.

Water absorption ability [g/g]=$B/A$ (2) Ratio of Water-Soluble Component

The gel obtained in the measurement of (1) Water Absorption Ability was dried in a hot air dryer set at 105° C. to a constant weight (C [g]), and the ratio of the water-soluble component was calculated according to the following formula. "A" is defined in the same manner as "A" in the measurement of (1) Water Absorption Ability.

Ratio of water-soluble component [% by mass]=$(A-C)/A \times 100$ (3) Melt Viscosity The measurement was executed for 1.5 g of the water-absorbent modified polyalkylene oxide or the like by means of a flow tester (constant test force extrusion type capillary rheometer, manufactured by Shimadzu Corporation, Model: CFT-500C) under the following conditions.

Load: 5.0 MPa
Measurement Temperature: 170° C.
Die Diameter: 1 mm
Die Length: 1 mm (4) Swelling Ratio The sheets of the lubricating resin composition obtained in Examples and Comparative Examples were each cut into a sheet of 2 cm (W)×5 cm (L) to be used as a measurement sample.

The mass (E [g]) of the measurement sample was measured, and the sample was then immersed in 100 [mL] of ion exchange water measured in a 200-mL beaker under room temperature (22° C.) for 24 hours to swell. The measurement sample was then taken out, and the water on the sample surface was wiped off with a paper towel to measure the mass (F [g]) thereof. When the swelling ratio is lower than 500%, it can be determined that the variation in dimensions due to swelling is small.

Swelling Ratio [%]=$(F-E)/E \times 100$ (5) Thickness Variation

The thickness (D2) was measured for the sample whose swelling ratio was measured, and was divided by the original thickness (D1) to obtain the thickness variation. When the thickness variation is equal to or smaller than four times, it can be determined that the variation is small.

Thickness Variation [times]=$D2/D1$ (6) Slimy Feeling

The sheets of the lubricating resin composition obtained in Examples and Comparative Examples were each cut into a sheet of 2 cm (W)×5 cm (L) to be used as a measurement sample.

Each of the measurement samples obtained in Examples or the like was immersed in 100 mL of ion exchange water measured in a 200-mL beaker for 1 minute, and the water on the sample surface was then wiped off with a paper towel.

The surface of the measurement sample was rubbed with hand, and the evaluation was executed according to the following evaluation criteria.

Evaluation Criteria
A: No slimy feeling was felt.
B: No cobwebbing occurred while slimy feeling was felt.
C: Slimy feeling was felt and cobwebbing occurred.

(7) Friction Physical Property

The sheets of the lubricating resin composition obtained in Examples and Comparative Examples were each cut into a sheet of 2 cm (N)×5 cm (L) to be used as a measurement sample.

0.2 mL of ion exchange water was added dropwise onto a coating surface of each of the measurement samples, and the measurement samples were left still for 30 seconds, 5 minutes, or 10 minutes under the conditions of 25° C. and 60% R.H. The friction coefficient μ was then monitored by means of a friction tester (manufactured by KATO TECH CO., LTD., Model: KES-SE) under the following test conditions (first monitoring).

Sensor: silicone
Load: 50 [g]
Velocity: 10 [mm/sec]

(i) Mean Coefficient of Friction (MIU) (Lubricity)

The mean coefficient of friction has correlation with ease of slipping and resistance against slipping felt in rubbing the surface. The surface is more difficult to slip on as the value become greater.

A schematic view is shown in FIG. 1 for obtaining a mean coefficient of friction (MIU) from a result of the monitoring of friction coefficient μ.

As shown in FIG. 1, the surface of the measurement sample is scanned for monitoring friction coefficient μ of the surface. The friction coefficient μ is integrated for a width of 20 mm for the monitoring (shaded area of FIG. 1). The mean coefficient of friction (MIU) is obtained by dividing the integral value by the width (20 mm) for the monitoring.

When the value of MIU is 0.10 or lower, the value is in such a range that no problem arises in the practical use. When the value is 0.02 or lower, its lubricity is good. When the value is 0.01 or lower, its lubricity is best.

(ii) Deviation in Mean Coefficient of Friction (MMD) (Roughness Resistant Property)

The deviation in the mean coefficient of friction has correlation with smoothness and roughness felt in rubbing the surface. The surface is rougher as this value becomes greater.

Figure 2:
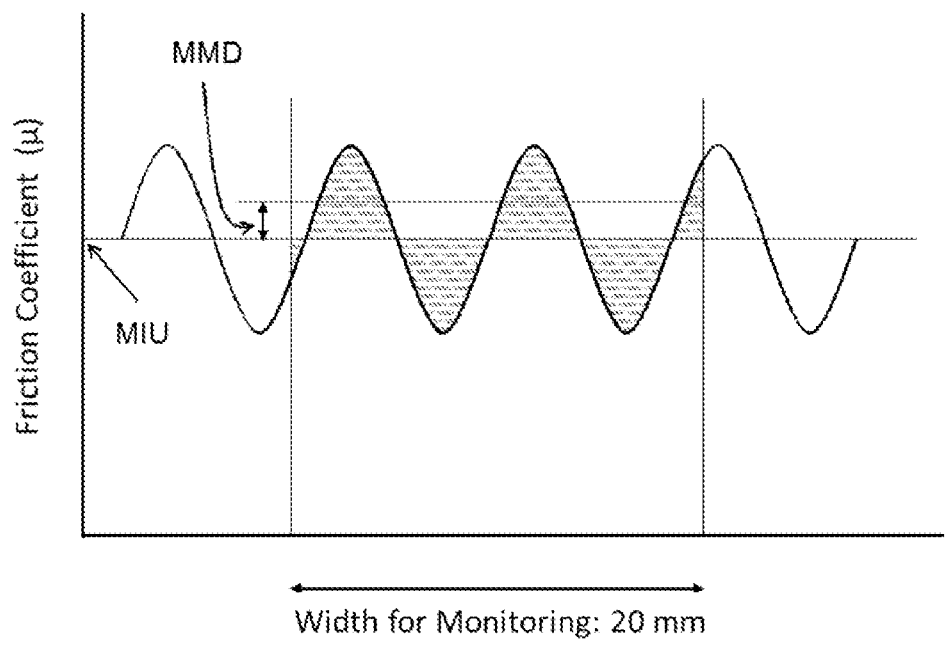
FIG. 2 is a schematic diagram of a method of determining a deviation in the mean coefficient of friction (MMD).

A schematic diagram is shown in FIG. 2 for determining the deviation in the mean coefficient of friction (MMD) from results of the monitoring of the friction coefficient.

As shown in FIG. 2, an absolute value of a difference between the mean coefficient of friction (MIU) and the friction coefficient μ is integrated for the width of 20 mm for monitoring (shaded area of FIG. 2). The deviation in the mean coefficient of friction (MMD) is obtained by dividing the integral value by the width for the monitoring (20 mm).

When the value of MMD is from 0.001 to 0.015, the smoothness of the surface is good.

When the value of MMD is 0.015 or lower, the value is in such a range that no problem arises in the practical use. When the value is 0.010 or lower, the smoothness of the surface is good. When the value of MMD is 0.005 or lower, the smoothness of the surface is best.

(iii) Repetition Test

After the first monitoring, the sheet was placed in an oven whose temperature was set at 50° C. for one hour to dry. Second monitoring was then performed under the same conditions as mentioned above. The monitoring was repeated up to a sixth time with the same procedure, and the mean coefficient of friction and its deviation were determined.

Production Example 1: Production of Water-Absorbent Modified Polyalkylene Oxide

One hundred parts by mass of a fully dehydrated polyethylene oxide having a number average molecular weight of 20,000, 0.90 parts by mass of 1,4-butanediol and 0.1 part by mass of dioctyltin dilaurate were put at these ratios into storage tank A equipped with a stirrer and held at 80° C., and were stirred in a nitrogen gas atmosphere to obtain a uniform mixture. Separately, dicycrohexylmethane-4,4'-diisocyanate was put into storage tank B held at 30° C., and was stored in a nitrogen gas atmosphere.

The mixture in storage tank A was continuously supplied at a rate of 500 [g/min], and dicyclohexylmetahane-4,4'-disisocyanate in storage tank B was continuously supplied at a rate of 19.4 [g/min] to a twin-screw extruder set at 110 to 140° C. (R value=1.00) by means of a metering pump, and these were mixed in the extruder to perform a reaction. A strand was then discharged through an exit of the extruder, and was pelletized (into blocks each of 4×4×2.5 mm) by means of a pelletizer to obtain a water-absorbent modified polyalkylene oxide.

The obtained water-absorbent modified polyalkylene oxide had a water absorption ability of 25 [g/g], a ratio of the water-soluble component of 15.5 [% by mass], and a melt viscosity of 320 [Pa·s]

Production Example 2: Production of Water-Absorbent Modified Polyalkylene Oxide

An ethylene oxide/propylene oxide (mass ratio: 90/10) copolymer having a number average molecular weight of 15000 was supplied at a rate of 250 [g/min], and ethylene Glycol heated to 40° C. was supplied at a rate of 2.1 [g/min] to a single-screw extruder having a diameter of 40 mm (L/D=40, preset temperature: 90° C.), and these were melt-mixed.

The mixture obtained from a discharge opening (the mixture was discharged in a uniform and molten state, and it was confirmed using an LC analysis that the mixture was mixed at the charge ratio) was continuously supplied to a hopper port (preset temperature: 80° C.) of a twin-screw extruder having a diameter of 30 mm (L/D=41.5). Simultaneously, dioctyltin dilaurate was supplied to the hopper port of the twin-screw extruder at a rate of 0.5 [g/min].

Separately, dicyclohexylmethane-4,4'-diisocyanate adjusted to 30° C. was supplied to a screw barrel section situated on the downstream side of the hopper port of the twin-screw extruder at a rate of 12.4 [g/min] (R value=0.95), and was thereby caused to continuously react under a nitrogen gas atmosphere (preset temperature: 180° C.). A strand obtained from the exit of the twin-screw extruder was cooled, and was then pelletized (into blocks each of 4×4×2.5 mm) by means of a pelletizer to obtain a water-absorbent modified polyalkylene oxide.

The obtained water-absorbent modified polyalkylene oxide had a water absorption ability of 20 [g/g], a ratio of the water-soluble component of 11.3 [6 by mass], and a melt viscosity of 150 [Pa·s]

Production Example 3: Production of Water-Absorbent Modified Polyalkylene Oxide

A polyethylene oxide having a number average molecular weight of 10000 was supplied at a rate of 200 [g/min], and 1,4-butanediol heated to 40° C. was supplied at a rate of 8.1 [g/min] to a single-screw extruder having a diameter of 40 mm (L/D=40, preset temperature: 90° C.), and these were melt-mixed.

The mixture obtained from a discharge port (the mixture was discharged in a uniform and molten state, and it was confirmed using an LC analysis that the mixture were mixed at the charge ratio) was continuously supplied to a hopper port (preset temperature: 80° C.) of a twin-screw extruder having a diameter of 30 mm (L/D=41.5). Simultaneously, dioctyltin dilaurate was supplied to the hopper port of the twin-screw extruder at a rate of 0.5 [g/min]

Separately, dicyclohexylmethane-4,4'-diisocyanate adjusted to 30° C. was supplied to a screw barrel section situated on the downstream side of the hopper port of the twin-screw extruder at a rate of 28.8 [g/min] (R value=1.00) and was caused to continuously react in a nitrogen gas atmosphere (preset temperature: 180° C.). A strand obtained from an exit of the twin-screw extruder was cooled and, then pelletized (into blocks each of 4×4×2.5 mm) by means of a pelletizer to obtain a water-absorbent modified polyalkylene oxide.

The obtained water-absorbent modified polyalkylene oxide had a water absorption ability of 7 [g/g], a ratio of the water-soluble component of 5.5 [% by mass], and a melt viscosity of 520 [Pa·s]

Production Example 4: Production of Water-Absorbent Modified Polyalkylene Oxide

One hundred parts by mass of a fully dehydrated polyethylene oxide having a number average molecular weight of 20000, 0.14 parts by mass of 1,4-butanediol and 0.1 part by mass of dioctyltin dilaurate were put at these ratios into storage tank A equipped with a stirrer and held at 80° C., and were stirred in a nitrogen gas atmosphere to obtain a uniform mixture. Separately, dicycrohexylmethane-4,4'-diisocyanate was put into storage tank B held at 30° C., and was stored in a nitrogen gas atmosphere.

The mixture in storage tank A was continuously supplied at a rate of 500 [g/min], and dicyclohexylmetahane-4,4'-disisocyanate in storage tank B was continuously supplied at a rate of 7.2 [g/min] to a twin-screw extruder set at 110 to 140° C. (R value=1.00) by means of a metering pump, and these were mixed in the extruder to perform a reaction. A strand was discharged through an exit of the extruder, and was pelletized (into blocks each of 4×4×2.5 mm) by means of a pelletizer to obtain a water-absorbent modified polyalkylene oxide.

The obtained water-absorbent modified polyalkylene oxide had a water absorption ability of 45 [g/g], a ratio of the water-soluble component of 38.5 [1 by mass], and a melt viscosity of 300 [Pa·s]

TABLE 1

| | Polyalkylene Oxide | | Diol | | | | Diisocyanate | |
|---|---|---|---|---|---|---|---|---|
| | Type | Used Amount (parts by mass) | Molecular Weight | Type (carbon number) | Molecular Weight | Molar Ratio[1] | Used Amount (parts by mass) | Type | Molecular Weight |
| Production Example 1 | EO | 100 | 20000 | 4 | 90 | 2 | 0.9 | HMDI | 262 |
| Production Example 2 | EO/PO | 250 | 15000 | 2 | 62 | 2 | 2.07 | HMDI | 262 |
| Production Example 3 | EO | 200 | 10000 | 4 | 90 | 4.5 | 8.1 | HMDI | 262 |
| Production Example 4 | EO | 100 | 20000 | 4 | 90 | 0.3 | 0.135 | IPDI | 222 |

| | Diisocyanate | | | | |
|---|---|---|---|---|---|
| | NCO/OH[2] | Used Amount (parts by mass) | Water Absorption Ability [g/g] | Water Soluble Component [%] | Melt Viscosity [Pa·s] |
| Production Example 1 | 1 | 3.93 | 25 | 16.6 | 320 |
| Production Example 2 | 0.95 | 12.445 | 20 | 11.3 | 150 |
| Production Example 3 | 1 | 28.82 | 7 | 5.5 | 520 |
| Production Example 4 | 1 | 1.443 | 45 | 38.5 | 300 |

[1]Molar ratio of used amount of diol relative to 1 mol of polyalkylene oxide
[2]Ratio of molar number of NCO groups in diisocyanate compound relative to total molar number of terminal OH groups in polyalkylene oxide and OH groups in diol Example 1

A water-absorbent modified polyalkylene oxide obtained in the same manner as in Production Example 1 was supplied at 6 [kg/hr] and a low-melting point polyamide resin [abbreviation: PAco, manufactured by EMS-CHEMIE (Japan), Ltd., Griltex D1500A, melting point 95° C., MFR=70 g/10 min (160° C., 21.18 N), melt viscosity 85 Pa·s] was supplied at 9 [kg/hr] to a twin-screw extruder having a diameter of 28 mm (L/D=40) set at 110° C. to obtain a lubricating resin composition. The compositional ratios of the lubricating resin composition are shown in Table 2.

The obtained lubricating resin composition was molded into a 10 cm×10 cm×0.1 cm sheet by means of a hot press (manufactured by Gonna Hydraulic Press Manufacturing Co., Ltd., 40-t press, pressure: 4.9 MPa·G) set at 120° C.

The obtained sheet of the lubricating resin composition was cut into a predetermined size, and the above various types of measurement and evaluation were executed therefor. The results thereof are shown in Table 2.

Example 2

A water-absorbent modified polyalkylene oxide obtained in the same manner as in Production Example 2 was supplied at 7 [kg/hr] and a low-melting point polyamide resin [abbreviation: PAco, manufactured by EMS-CHEMIE (Japan), Ltd., Griltex D1500A, melting point 95° C., MFR=70 g/10 min (160° C., 21.18 N), melt viscosity 85 Pa·s] was supplied at 17.5 [kg/hr] to a twin-screw extruder having a diameter of 28 mm (L/D=40) set at 120° C. to obtain a lubricating resin composition. The compositional ratios of the lubricating resin composition are shown in Table 2.

The obtained lubricating resin composition was molded into a 10 cm×10 cm×0.1 cm sheet by means of a hot press (manufactured by Gonno Hydraulic Press Manufacturing Co., Ltd., 40-t press, pressure: 4.9 MPa·G) set at 120° C.

The obtained sheet of the lubricating resin composition was cut into a predetermined size and the above various types of measurement and evaluation were executed therefor. The results thereof are shown in Table 2.

Example 3

A water-absorbent modified polyalkylene oxide obtained in the same manner as in Production Example 1 was supplied at 5 [kg/hr] and a low-melting point polyamide resin [abbreviation: PAco, manufactured by EMS-CHEMIE (Japan), Ltd., Griltex D1666A, melting point 85° C., MFR=90 g/10 min (160° C., 21.18 N), melt viscosity 55 Pa·s] was supplied at 17.5 [kg/hr] to a twin-screw extruder having a diameter of 28 mm (L/D=40) set at 130° C. to obtain a lubricating resin composition. The compositional ratios of the lubricating resin composition are shown in Table 2.

The obtained lubricating resin composition was molded into a 10 cm (W)×10 cm (L)×0.1 cm (T) sheet of the lubricating resin composition by means of a hot press (manufactured by Gonno Hydraulic Press Manufacturing Co., Ltd., 40-t press, pressure: 4.9 MPa·G) set at 130° C.

The obtained sheet of the lubricating resin composition was cut into a predetermined size and the above various types of measurement and evaluation were executed therefor. The results thereof are shown in Table 2.

Example 4

A water-absorbent modified polyalkylene oxide obtained in the same manner as in Production Example 2 was supplied at 7.5 [kg/hr] and a low-melting point polyamide resin [abbreviation: PAco, manufactured by EMS-CHEMIE (Japan), Ltd., Griltex D1500A, melting point 95° C., MFR=70 g/10 min (160° C., 21.18 N), melt viscosity 85 Pa·s] was supplied at 7.5 [kg/hr] to a twin-screw extruder having a diameter of 28 mm (L/D=40) set at 120° C. to obtain a lubricating resin composition. The compositional ratios of the lubricating resin composition are shown in Table 2.

The obtained lubricating resin composition was molded into a 10 cm×10 cm×0.1 cm sheet by means of a hot press (manufactured by Gonna Hydraulic Press Manufacturing Co., Ltd., 40-t press, pressure: 4.9 MPa·G) set at 120° C.

The obtained sheet of the lubricating resin composition was cut into a predetermined size and the above various types of measurement and evaluation were executed therefor. The results thereof are shown in Table 2.

Examples 5 to 7

Lubricating resin compositions were obtained in the same manner as in Example 1 except that low-melting point polyamide resins described below were used, that the preset temperature of the twin-screw extruder having a diameter of 28 mm was changed to the temperatures described below, and/or that the blending amount of the low-melting point polyamide was changed as shown in Table 2.

Molding of the lubricating resin composition into the sheet and the types of measurement and evaluation were executed in the same manner as in Example 1 except that the pressing temperature was changed to the values below.

Example 5

Low-Melting Point Polyamide Resin

[Abbreviation: PAco, manufactured by EMS-CHEMIE (Japan), Ltd., Griltex 1A, melting point 115° C., MFR=16/ 10 min (160° C., 21.18 N), melt viscosity 120 Pa·s]
Preset Temperature of Twin-Screw Extruder: 140° C.
Pressing Temperature: 140° C.

Example 6

Low-Melting Point Polyamide Resin

[Abbreviation: PAco, manufactured by EMS-CHEMIE (Japan), Ltd., Griltex 2A, melting point 130° C., MFR=18 g/10 min (160° C., 21.18 N), melt viscosity 135 Pa·s]
Preset Temperature of Twin-Screw Extruder: 140° C.
Pressing Temperature: 140° C.

Example 7

Low-Melting Point Polyamide Resin

[Abbreviation: PAco, manufactured by EMS-CHEMIE (Japan), Ltd., Griltex D1500A, melting point 95° C., MFR=70 g/10 min (160° C., 21.18 N), melt viscosity 85 Pa·s]
Preset Temperature of Twin-Screw Extruder: 120° C.
Pressing Temperature: 120° C.

Comparative Example 1

A water-absorbent modified polyalkylene oxide obtained in the same manner as in Production Example 1 was supplied at 12.5 [kg/hr] and a low-melting point polyamide resin [abbreviation: PAco, manufactured by EMS-CHEMIE (Japan), Ltd., Griltex D1500A, melting point 95° C., MFR=70 g/10 min (160° C., 21.18 N), melt viscosity 85 Pa·s] was supplied at 2.5 [kg/hr] to a twin-screw extruder having a diameter of 28 mm set at 120° C. to obtain a lubricating resin composition. The compositional ratios of the lubricating resin composition are shown in Table 3.

The obtained lubricating resin composition was molded into a 6 cm (W)×9 cm (L)×0.15 cm (T) sheet of the lubricating resin composition by means of an injection-molding machine (manufactured by Toyo Machinery and Metal Co., Ltd., Model: T180G2) set at 130 to 150° C.

The obtained sheet of the lubricating resin composition was cut into a predetermined size and the above various types of measurement and evaluation were executed therefor. The results thereof are shown in Table 3.

Comparative Example 2

A water-absorbent modified polyalkylene oxide obtained in the same manner as in Production Example 2 was supplied at 6 [kg/hr] and an ethylene/vinyl acetate copolymer [abbreviation: EVA, manufactured by Du Pont-Mitsui Fluorochemicals Co, Ltd.: Evaflex EV150, vinyl acetate content=33%, melting point=MFR=30 g/10 min (190° C., 21.18 N), melt viscosity 170 Pa·s] was supplied at 15 [kg/hr] to a twin-screw extruder having a diameter of 28 mm (L/D=40) set at 140° C. to obtain a lubricating resin composition. The compositional ratios of the lubricating resin composition are shown in Table 3.

The obtained lubricating resin composition was molded into a 10 cm (W)×10 cm (L)×0.1 cm (T) sheet of the lubricating resin composition by means of the hot press (manufactured by Gonno Hydraulic Press Manufacturing Co., Ltd., 40-t press, pressure: 4.9 MPa·G) set at 150° C.

The obtained sheet of the lubricating resin composition was cut into a predetermined size and the above various types of measurement and evaluation were executed therefor. The results thereof are shown in Table 3.

Comparative Example 3

A water-absorbent modified polyalkylene oxide obtained in the same manner as in Production Example 2 was supplied at 6 [kg/hr] and a high impact polystyrene [abbreviation: HIPS, manufactured by PS Japan Corporation, MFR=18 g/10 min (200° C., 49.03 N), melt viscosity unmeasurable] was supplied at 15 [kg/hr] to a twin-screw extruder having a diameter of 28 mm (L/D=40) set at 220° C. to obtain a lubricating resin composition. The compositional ratios of the lubricating resin composition are shown in Table 3.

The obtained lubricating resin composition was molded into a 10 cm (W)×10 cm (L)×0.1 cm (T) sheet of the lubricating resin composition by means of a hot press (manufactured by Gonno Hydraulic Press Manufacturing Co., Ltd., 40-t press, pressure: 4.9 MPa·G) set at 220° C.

The obtained sheet of the lubricating resin composition was cut into a predetermined size and the above various types of measurement and evaluation were executed therefor. The results thereof are shown in Table 3.

Comparative Examples 4 to 7

Lubricating resin compositions were obtained in the same manner as in Example 1 except that the modified polyalkylene oxide was changed to those obtained in Production Examples described in Table 3, that low-melting point polyamide resins described below were used, that the preset temperature of the twin-screw extruder having a diameter of 28 mm was changed to the values described below, and/or that the blending amount of the low-melting point polyamide was changed to values shown in Table 3.

Molding of the lubricating resin composition into the sheet and the types of measurement and evaluation were executed in the same manner as in Example 1 except that the pressing temperature was changed to the values below.

Comparative Example 4

Modified Polyalkylene Oxide: Production Example 3

Low-Melting Point Polyamide Resin

[abbreviation: PAco, manufactured by EMS-CHEMIE (Japan), Ltd., Griltex D1500A, melting point 95° C., MFR=70 g/10 min (160° C., 21.18 N), melt viscosity 85 Pa·s]
Preset Temperature of Twin-Screw Extruder: 120° C.
Pressing Temperature: 120° C.

Comparative Example 5

Modified Polyalkylene Oxide: Production Example 4

Low-Melting Point Polyamide Resin

[abbreviation: PAco, manufactured by EMS-CHEMIE (Japan), Ltd., Griltex D1500A, melting point 95° C., MFR=70 g/10 min (160° C., 21.18 N), melt viscosity 85 Pa·s]
Preset Temperature of Twin-Screw Extruder: 120° C.
Pressing Temperature: 120° C.

Comparative Example 6

Modified Polyalkylene Oxide: Production Example 1

Polyamide Resin

[abbreviation: PAco, manufactured by Toray Industries, Inc., Amilan CM6041CF melting point 194° C., melt viscosity unmeasurable]
Preset Temperature of Twin-Screw Extruder: 220° C.
Pressing Temperature: 220° C.

Comparative Example 7

Modified Polyalkylene Oxide: Production Example 1

Low-Melting Point Polyamide Resin

[abbreviation: PAco, manufactured by EMS-CHEMIE (Japan), Ltd., Griltex D1500A, melting point 95° C., MFR=70 g/10 min (160° C., 21.18 N), melt viscosity 85 Pa·s]
Preset Temperature of Twin-Screw Extruder: 120° C.
Pressing Temperature: 120° C.

TABLE 2

| | Modified Polyalkylene Oxide | | | Thermostatic Resin[1] | | | | | | |
|---|---|---|---|---|---|---|---|---|---|---|
| | | Water Absorption Ability [g/g] | Melt Viscosity [Pa·s] | Type | Melting Point (° C.) | MFR [g/10 min] | Melt Viscosity [Pa·s] | (parts by mass)[2] | Swelling Ratio (%) | Thickness Variation [times] | Slimy Feeling |
| | Type | | | | | | | | | | |
| Example 1 | Production Example 1 | 25 | 320 | PAco | 95 | 70 (160° C., 21.18N) | 85 | 180 | 370 | 2.5 | A |
| Example 2 | Production Example 2 | 20 | 150 | PAco | 95 | 70 (160° C., 21.18N) | 85 | 250 | 170 | 1.8 | A |
| Example 3 | Production Example 1 | 25 | 320 | PAco | 85 | 80 (160° C., 21.18N) | 85 | 350 | 120 | 1.2 | A |
| Example 4 | Producation Example 2 | 20 | 180 | PAco | 95 | 20 (160° C., 21.18N) | 85 | 100 | 480 | 3.5 | A |
| Example 5 | Production Example 1 | 25 | 320 | PAco | 115 | 18 (160° C., 21.18N) | 120 | 150 | 300 | 1.8 | A |
| Example 6 | Production Example 1 | 25 | 320 | PAco | 130 | 18 (160° C., 21.18N) | 135 | 150 | 280 | 1.5 | A |
| Example 7 | Production Example 1 | 25 | 280 | PAco | 95 | 70 (160° C., 21.18N) | 85 | 50 | 480 | 3.6 | A |

TABLE 2-continued

| | Friction Physical Property | | | | | | | | | | | |
|---|---|---|---|---|---|---|---|---|---|---|---|---|
| | Mass Coefficient of Friction (MU) (Lubricity) | | | | | | Deviation on Mass Coefficient of Friction (MMD) (Roughness Resistant Property) | | | | | |
| | First Time | | | Sixth Time | | | First Time | | | Sixth Time | | |
| | 30 sec | 5 min | 10 min | 30 sec | 8 min | 10 min | 30 sec | 5 min | 10 min | 30 sec | 5 min | 10 min |
| Example 1 | 0.01 | 0.01 | 0.01 | 0.01 | 0.01 | 0.01 | 0.004 | 0.004 | 0.004 | 0.004 | 0.004 | 0.004 |
| Example 2 | 0.015 | 0.015 | 0.015 | 0.015 | 0.015 | 0.015 | 0.009 | 0.009 | 0.009 | 0.009 | 0.009 | 0.009 |
| Example 3 | 0.02 | 0.02 | 0.02 | 0.02 | 0.02 | 0.02 | 0.008 | 0.008 | 0.008 | 0.008 | 0.008 | 0.008 |
| Example 4 | 0.01 | 0.01 | 0.01 | 0.01 | 0.01 | 0.01 | 0.008 | 0.008 | 0.008 | 0.008 | 0.008 | 0.006 |
| Example 5 | 0.013 | 0.013 | 0.013 | 0.013 | 0.013 | 0.013 | 0.009 | 0.009 | 0.009 | 0.009 | 0.009 | 0.009 |
| Example 6 | 0.015 | 0.015 | 0.015 | 0.015 | 0.015 | 0.015 | 0.008 | 0.008 | 0.008 | 0.008 | 0.008 | 0.008 |
| Example 7 | 0.01 | 0.01 | 0.01 | 0.01 | 0.01 | 0.01 | 0.008 | 0.008 | 0.008 | 0.008 | 0.008 | 0.008 |

[1]PAco: Copolymerized Nylon, EVA: Ethylene/Vinyl Acetate Copolymer: HIPS: High Impact Polystyrene
[2]Parts by mass of thermoplastic resin relative to 100 parts by mass of modified polyalkyline oxide

TABLE 3

| | Modified Polyalkylene Oxide | | | Thermostatic Resin[1] | | | | | | | |
|---|---|---|---|---|---|---|---|---|---|---|---|
| | Type | Water Absorption Ability [g/g] | Melt Viscosity [Pa·s] | Type | Melting Point (° C.) | MFR [g/10 min] | Melt Viscosity [Pa·s] | (parts by mass)[2] | Swelling Ratio (%) | Thickness Variation [times] | Slimy Feeling |
| Comparative Example 1 | Production Example 1 | 25 | 320 | PAco | 95 | 70 (160° C., 21.18N) | 85 | 20 | 1250 | 3.3 | A |
| Comparative Example 2 | Production Example 2 | 20 | 150 | EVA | — | 30 (190° C., 21.18N) | 170 | 250 | 250 | 2.5 | A |
| Comparative Example 3 | Production Example 1 | 20 | 150 | HIPS | — | 18 (200° C., 49.03N) | 85 | 250 | 110 | 1.1 | A |
| Comparative Example 4 | Producation Example 2 | 7 | 150 | PAco | 93 | 70 (160° C., 21.18N) | 85 | 150 | 110 | 1.1 | A |
| Comparative Example 5 | Production Example 1 | 45 | 300 | PAco | 95 | 70 (160° C., 21.18N) | 85 | 150 | 550 | 4.2 | C |
| Comparative Example 6 | Production Example 1 | 25 | 320 | PAco | 194 | — | — | 150 | 100 | 1.1 | A |
| Comparative Example 7 | Production Example 1 | 25 | 320 | PAco | 95 | 70 (160° C., 21.18N) | 85 | 550 | 110 | 1.1 | A |

| | Friction Physical Property | | | | | | | | | | | |
|---|---|---|---|---|---|---|---|---|---|---|---|---|
| | Mass Coefficient of Friction (MU) (Lubricity) | | | | | | Deviation on Mass Coefficient of Friction (MMD) (Roughness Resistant Property) | | | | | |
| | First Time | | | Sixth Time | | | First Time | | | Sixth Time | | |
| | 30 sec | 5 min | 10 min | 30 sec | 5 min | 10 min | 30 sec | 5 min | 10 min | 30 sec | 5 min | 10 min |
| Comparative Example 1 | 0.01 | 0.01 | 0.01 | 0.01 | 0.01 | 0.01 | 0.009 | 0.009 | 0.009 | 0.009 | 0.009 | 0.009 |
| Comparative Example 2 | 0.12 | 0.16 | 0.23 | 0.18 | 0.17 | 0.23 | 0.03 | 0.05 | 0.06 | 0.04 | 0.06 | 0.07 |
| Comparative Example 3 | 0.15 | 0.22 | 0.25 | 0.16 | 0.25 | 0.28 | 0.02 | 0.05 | 0.06 | 0.03 | 0.04 | 0.07 |
| Comparative Example 4 | 0.2 | 0.23 | 0.3 | 0.23 | 0.25 | 0.33 | 0.02 | 0.04 | 0.05 | 0.03 | 0.05 | 0.08 |
| Comparative Example 5 | 0.011 | 0.011 | 0.011 | 0.15 | 0.15 | 0.15 | 0.008 | 0.008 | 0.009 | 0.03 | 0.03 | 0.03 |
| Comparative Example 6 | 0.11 | 0.11 | 0.11 | 0.12 | 0.12 | 0.12 | 0.01 | 0.01 | 0.01 | 0.01 | 0.01 | 0.01 |
| Comparative Example 7 | 0.11 | 0.11 | 0.11 | 0.12 | 0.12 | 0.12 | 0.01 | 0.01 | 0.01 | 0.01 | 0.01 | 0.01 |

[1]Paco: Copolymerized Nylon, EVA: Ethylene/Vinyl Acetate Copolymer: HIPS: High Impact Polystyrene
[2]Parts by mass of thermoplastic resin relative to 100 parts by mass of modified polyalkyline oxide As is apparent from the results shown in Tables 2 and 3, the lubricating resin compositions of the present invention comprising each certain amounts of the water-absorbent modified polyalkylene oxide and the low-melting point polyamide resin have small variation in dimension due to swelling, and maintain the lubricity thereof and have no variation in roughness resistant property even under a wet condition, under a dry condition or during repeated use thereof.

INDUSTRIAL APPLICABILITY

The lubricating resin composition according to the present invention maintains its lubricity and represents no slimy feeling even under a wet or dry condition or during repeated use thereof, and can thus be suitably used in a wide field in which lubricity under a wet condition is necessary, for example, personal care items such as wet shaving instruments typified by a razor, and a catheter.

The invention claimed is:

1. A lubricating resin composition for personal care, wherein the composition comprises 100 parts by mass of a water-absorbent modified polyalkylene oxide and 50 to 400 parts by mass of a low-melting point polyamide resin, wherein the low-melting point polyamide resin is a polyamide resin having a melting point of 160° C. or lower,
wherein a water absorption ability of the water-absorbent modified polyalkylene oxide is 10 to 40 [g/g].

2. The lubricating resin composition for personal care according to claim 1, wherein
the water-absorbent modified polyalkylene oxide is a modified polyalkylene oxide obtained by reacting a polyalkylene oxide compound, a diol compound and a diisocyanate compound with each other.

3. The lubricating resin composition for personal care according to claim 1, wherein a ratio of a water-soluble component of the water-absorbent modified polyalkylene oxide is 5 to 30% by mass.

4. The lubricating resin composition for personal care according to claim 1, wherein the low-melting point polyamide resin is polyamide obtained by polymerizing raw materials comprising at least one type of raw material for polyamide selected from the group consisting of nylon 6, nylon 66, nylon 610, nylon 11, and nylon 12, or a combination of two or more types of the polyamide.

* * * * *